US008409615B2

(12) United States Patent
Dansereau et al.

(10) Patent No.: US 8,409,615 B2
(45) Date of Patent: *Apr. 2, 2013

(54) LOW DOSAGE FORMS OF RISEDRONATE OR ITS SALTS

(75) Inventors: Richard John Dansereau, Cincinnati, OH (US); David Ernest Burgio, Jr., Liberty Township, OH (US)

(73) Assignee: Warner Chilcott Company, LLC, Fajardo, PR (US)

( * ) Notice: Subject to any disclaimer, the term of this patent is extended or adjusted under 35 U.S.C. 154(b) by 249 days.

This patent is subject to a terminal disclaimer.

(21) Appl. No.: 12/638,359

(22) Filed: Dec. 15, 2009

(65) Prior Publication Data

US 2010/0113395 A1    May 6, 2010

Related U.S. Application Data

(63) Continuation of application No. 12/183,359, filed on Jul. 31, 2008, now abandoned, which is a continuation-in-part of application No. 11/286,875, filed on Nov. 23, 2005, now Pat. No. 7,645,460, which is a continuation-in-part of application No. 11/106,816, filed on Apr. 15, 2005, now Pat. No. 7,645,459.

(60) Provisional application No. 60/573,881, filed on May 24, 2004.

(51) Int. Cl.
*A61K 9/28*      (2006.01)

(52) U.S. Cl. ............ 424/474; 424/465; 424/468; 514/89

(58) Field of Classification Search .................... 424/474
See application file for complete search history.

(56) References Cited

U.S. PATENT DOCUMENTS

| | | | |
|---|---|---|---|
| 5,167,947 A | 12/1992 | Geary | |
| 5,296,475 A | 3/1994 | Flesch et al. | 514/108 |
| 5,304,377 A | 4/1994 | Yamada et al. | 424/426 |
| 5,356,887 A | 10/1994 | Brenner et al. | |
| 5,431,920 A | 7/1995 | Bechard | 424/480 |
| 5,438,048 A | 8/1995 | Nikander et al. | |
| 5,462,932 A | 10/1995 | Brenner et al. | 514/108 |
| 5,622,721 A | 4/1997 | Dansereau et al. | 424/490 |
| 5,686,106 A | 11/1997 | Kelm et al. | 424/463 |
| 5,735,810 A | 4/1998 | Sage, Jr. et al. | |
| 5,853,759 A | 12/1998 | Katdare et al. | 424/466 |
| 5,935,602 A | 8/1999 | Dansereau et al. | |
| 6,143,326 A | 11/2000 | Mockel et al. | 424/482 |
| 6,200,602 B1 | 3/2001 | Watts et al. | 424/463 |
| 6,248,363 B1 | 6/2001 | Patel et al. | 424/497 |
| 6,309,663 B1 | 10/2001 | Patel et al. | 424/450 |
| 6,333,316 B1 | 12/2001 | Daifotis et al. | 514/108 |
| 6,368,629 B1 | 4/2002 | Watanabe et al. | 424/482 |
| 6,416,737 B1 | 7/2002 | Manolagas et al. | |
| 6,432,932 B1 | 8/2002 | Daifotis et al. | 514/108 |
| 6,468,559 B1 | 10/2002 | Chen et al. | |
| 6,506,407 B2 | 1/2003 | Watanabe et al. | 424/463 |
| 6,623,755 B2 | 9/2003 | Chen et al. | 424/464 |
| 6,676,965 B1 | 1/2004 | Lulla et al. | 424/458 |
| 6,677,320 B2 | 1/2004 | Diederich et al. | 514/102 |
| 7,309,698 B2 | 12/2007 | Boyd et al. | 514/102 |
| 7,645,459 B2 | 1/2010 | Dansereau et al. | 424/474 |
| 7,645,460 B2 | 1/2010 | Dansereau et al. | 424/474 |
| 2001/0036475 A1 | 11/2001 | Chen et al. | 424/465 |
| 2003/0158154 A1 | 8/2003 | Flashner-Barak | 514/89 |
| 2003/0203878 A1 | 10/2003 | Flashner-Barak et al. | 514/89 |
| 2005/0070504 A1 | 3/2005 | Burgio et al. | |
| 2005/0089573 A1 | 4/2005 | Moeckel et al. | 424/471 |
| 2005/0182028 A1 | 8/2005 | Chen | 514/89 |
| 2005/0226907 A1 | 10/2005 | Moneymaker et al. | 424/439 |
| 2005/0260262 A1 | 11/2005 | Dansereau et al. | 424/464 |
| 2006/0069069 A1 | 3/2006 | Kajander et al. | 514/89 |
| 2006/0110452 A1 | 5/2006 | Dansereau et al. | 424/464 |
| 2006/0134190 A1 | 6/2006 | Kim et al. | 424/451 |
| 2006/0210639 A1 | 9/2006 | Liversidge et al. | 424/489 |
| 2006/0263355 A1 | 11/2006 | Quan et al. | 424/141.1 |
| 2007/0003512 A1 | 1/2007 | Stockel et al. | 424/76.1 |
| 2007/0238707 A1 | 10/2007 | Leonard | 514/89 |
| 2008/0286359 A1 | 11/2008 | Dansereau et al. | 424/474 |
| 2008/0287400 A1 | 11/2008 | Dansereau et al. | 514/87 |

FOREIGN PATENT DOCUMENTS

| | | |
|---|---|---|
| BR | 106601-3 | 9/2003 |
| EP | 0449405 A2 | 10/1991 |
| IN | 2004MU01360 A | 7/2006 |
| JP | 7-501073 T | 2/1995 |
| JP | 8092102 | 4/1996 |
| JP | 9-504276 T | 4/1997 |
| WO | WO 93/09785 | 5/1993 |
| WO | WO 93/21907 | 11/1993 |
| WO | WO 97/44017 | 11/1997 |
| WO | WO 98/14196 A1 | 4/1998 |
| WO | WO 99/02539 A1 | 1/1999 |

(Continued)

OTHER PUBLICATIONS

Boulenc, X. et al., "Importance of the paracellular pathway for the transport of a new bisphosphonate using the human CACO-2 monolayers model," Biochemical Pharmacology, vol. 46, No. 9, pp. 1591-1600 (1993).

(Continued)

*Primary Examiner* — Jake M. Vu
(74) *Attorney, Agent, or Firm* — Fitzpatrick, Cella, Harper & Scinto

(57) ABSTRACT

Oral dosage forms comprising risedronate or a salt thereof, a chelating agent, and means for effecting delayed release of the risedronate (or salt) immediate release of the oral dosage form to the small intestine of the mammal subject and pharmaceutically effective absorption of the bisphosphonate with or without food or beverages. The present invention substantially alleviates the interaction between the risedronate (or salt) and food or beverages, which interaction results in the active ingredient not being available for absorption. The resulting oral dosage form may thus be taken with or without food. Further, disclosed is delivery of risedronate and the chelating agent to the small intestine, substantially alleviating the upper GI irritation associated with bisphosphonate therapies. These benefits simplify previously complex treatment regimens and can lead to increased patient compliance with bisphosphonate therapies.

19 Claims, No Drawings

FOREIGN PATENT DOCUMENTS

| | | |
|---|---|---|
| WO | WO 00/61111 | 10/2000 |
| WO | WO 01/02155 A1 | 2/2001 |
| WO | WO 01/32185 | 5/2001 |
| WO | WO 01/32185 A1 | 5/2001 |
| WO | WO 01/52859 | 7/2001 |
| WO | WO 01/76577 | 10/2001 |
| WO | WO 01/82903 | 11/2001 |
| WO | WO 03/002151 | 1/2003 |
| WO | WO 03/007916 | 1/2003 |
| WO | WO 03/051373 A1 | 6/2003 |
| WO | WO 2004/065397 | 8/2004 |
| WO | WO 2005/016872 | 5/2005 |
| WO | WO 2006/019843 | 2/2006 |
| WO | WO 2006/020009 | 2/2006 |

OTHER PUBLICATIONS

Boulenc, X. et al., "Bisphosphonates increase tight junction permeability in the human intestinal epithelial (Caco-2) model", International J. of Pharmaceutics, vol. 123, pp. 13-24 (1995).
Bronner, F. et al., "Nutritional Aspects of Calcium Absorption", J. Nutr., vol. 129, pp. 9-12 (1999).
Dowty, M. et al., APPS Annual Meeting, San Francisco, Nov. 19, 1998.
Ezra, A. et al., "Administration routes and delivery systems of bisphosphonates for the treatment of bone resorption", Drug Delivery Review, vol. 42, pp. 175-195 (2000).
Gertz, B.J. et al., "Studies of the oral bioavailability of alendronate", Clinical Pharmacology & Therapeutics, vol. 58, No. 3, pp. 288-298 (1995).
Green, J.R. et al., "The effect of zoledronate and pamidronate on the intestinal permeability barrier in vitro and in vivo", International J. of Pharmaceutics, vol. 153, pp. 59-66 (1997).
Janner, M. et al., "Sodium EDTA Enhances Intestinal Absorption of Two Bisphosphonates", Calcified Tissue International, vol. 49, pp. 280-283 (1991).
Kinget, R. et al., "Colonic drug targeting", J. of Drug Targeting, 1998, vol. 6, No. 2, pp. 129-149 (1998).
Lin, J.H. et al., "On the Absorption of Alendronate in Rats", J. of Pharmaceutical Sciences, vol. 83, No. 12, pp. 1741-1746 (1994).
Mahe, S. et al., "Gastroileal nitrogen and electrolyte movements after bovine milk ingestion in humans", Am. J. Clin. Nutr., vol. 56, pp. 410-416 (1992).
Mitchell, D. et al., "The effect of dosing regimen on the pharmacokinetics of risedronate", Br. J. Clin. Pharmacol., vol. 48, pp. 536-542 (1998).
Mitchell, D. et al., "Risedronate Gastrointestinal Absorption is Independent of Site and Rate of Administration", Pharm. Res., vol. 15, No. 2, pp. 228-232 (1998).
Muranishi, S., "Absorption Enhancers", Critical Reviews in Therapeutic Drug Carrier Systems, vol. 7, No. 1, pp. 1-33 (1990).
Nykanen, P. et al., "Citric acid as excipient in multiple-unit enteric-coated tablets for targeting drugs on the colon", International J. of Pharmaceutics, vol. 229, pp. 155-162 (2001).
Perez-Millan, "Subserosal Eosinophilic Gastroenteritis Treated Efficaciously with Sodium Cromoglycate," Digestive Diseases and Sciences, vol. 42, No. 2, (1997).
Poiger, H. et al., "Compensation of dietary induced reduction of teracycline absorption by simultaneous administration of EDTA", Europ. J. Clin. Pharmacol, vol. 14, pp. 129-131 (1978).
Raiman, J. et al., "Effects of various absorption enhancers on transport of clodronate through caco-2 cells," International Journal of Pharmaceutics, vol. 261, pp. 129-136 (2003).
Rowe, R.C. (Ed.), "Edetic Acid", Handbook of Pharmaceutical Excipients, pp. 225-228 (2002).
Simon, et al., "The effect of clodronate on the integrity and viability of rat small intestine in vitro—a comparison with EDTA," Biological Pharmaceutical Bulletin, vol. 28, No. 7, pp. 1249-1253. Journal code: 9311984. ISSN:0918-6158 (2005).
Swenson, E.S. et al., "(C) Means to enhance penetration (2) Intestinal permeability enhancement for proteins, peptides and other polar drugs: mechanisms and potential toxicity", Advanced Drug Deliver Reviews, vol. 8, pp. 39-92 (1992).
Tomita, M. et al., "Absorption-enhancing mechanism of EDTA, Caprate, and Decanoylcarnitine in Caco-2 cells", J. of pharmaceutical Sciences, vol. 85, No. 6, pp. 608-611 (1996).
Watts, P.J. et al., "Colonic drug delivery", Drug Development and Industrial Pharmacy, 1997, vol. 23, No. 9, pp. 893-913 (1997).
Whittaker, P. et al., "Toxicological profile, current use, and regulatory issues on EDTA compounds for assessing use of sodium iron EDTA for food fortification", Regulatory Toxicology and Pharmacology, vol. 18, pp. 419-427 (1993).
PCT International Search Report dated Dec. 7, 2005.
Katsuma et al., "Scintigraphic Evaluation of a Novel Colon-Targeted Delivery System (CODES-TM) in Healthy Volunteers," J. Pharm. Sci. 93(5) 1287-99 (2004).
Lin et al., "Factors Affecting Oral Absorption of Alendronate, a Potent Antiosteolytic Bisphosphonate in Rats," Pharm. Research, 8:S273 (1991).
Summons to Attend Oral Proceedings Pursuant to Rule 115(1) EPC in the Opposition against in related European Patent No. 1 753 395, 8 pages, mailed Mar. 23, 2012.
Vasikaran, "Bisphosphonates: an overview with special reference to alendronate," Ann. Clin. Biochem. 38:608-23 (2001).
Wasserman, "Vitamin D and the Dual Processes of Intestinal Calcium Absorption," J. Nutr., 134:3137-39 (2004).
Berne et al., Chapter 31: Gastrointestinal Regulation and Motility, pp. 539-565, Physiology, Mosby Publishing (5th Ed., 2004).
Fordtran et al., "Ionic Constituents and Osmolality of Gastric Emptying and Small-Intestinal Fluids after Eating," Am. J. Dig. Dis., 11:503-21 (1966).
Lindahl et al., "Characterization of Fluids from the Stomach and Proximal Jejunum in Men and Women," Pharm. Res., 14:497-502 (1997).
Phillips et al., "The Contribution of the Colon to Electrolyte and Water Conservation in Man," J. Lab. Clin. Med., 81:733-46 (1973).
Lenter, Gergy Scientific Tables, vol. 1: Units of Measurement, Body Fluids, Composition of the Body, Nutrition, pp. 123-158 (1981).
Fransson et al., "Distribution of Trace Elements and Minerals in Human and Cow's Milk," Ped. Res., 17:912-15 (1983).
Wilding et al., "The Role of Gamma Scintigraphy in Oral Drug Delivery," Adv. Drug. Delivery Rev., 7:87-117 (1991).
Rao et al., Chapter 25: The Stomach, Pylorus and Duodenum, pp. 373-392, An Illustrated Guide to Gastrointestinal Motility, Kumar and Wingate eds., Churchill Livingstone (2nd Ed., 1993).
Bueno et al., Chapter 10: Food and Gastrointestinal Motility, pp. 130-143, An Illustrated Guide to Gastrointestinal Motility, Kumar and Wingate eds., Churchill Livingstone (2nd Ed., 1993).
Lee et al. "MR Imaging of the Small Bowel Using the HASTE sequence," Am. J. Roentgenol., 170(6):1457-63 (1998).
Lachman, "Antioxidants and Chelating Agents as Stabilizers in Liquid Dosage Forms," The Indian Journal of Pharmacy, 30:109-119 (1968).
Skoog et al., The Fundamentals of Analytical Chemistry, pp. 281-283, Saunders College Publishing, (7th ed., 1996).
Lin, "Bisphosphonates: A Review of Their Pharmacokinetic Properties", Bone, 18:75-85 (1996).
Fleisch "Bisphosphonates in Bone Disease," Stampli & Co., Bern, p. 50 (1993).
Sakuma, "Effect of Administration Site in the Gastrointestinal Tract on Bioavailability of Poorly Absorbed Drugs Taken After Meal," J. Controlled Release, 118:59-64 (2007).
Lenter, Gergy Scientific Tables, vol. 1: Units of Measurement, Body Fluids, Composition of the Body, Nutrition, pp. 241-266 (1981).
World Health Organization Technical Report Series No. 539, Toxicological Evaluation of Certain Food Additives with a Review of General Principles and of Specifications, Seventeenth Report of the Joint FAO/WHO Expert Committee on Food Additives, pp. 1-40 (1974).
Guidance for Industry and Reviewers. Estimating the Safe Starting Dose in Clinical Trials for Therapeutics in Adult Healthy Volunteers, Draft Guidance, pp. 1-26 (Dec. 2002).
Guidance for Industry. Estimating the Maximum Safe Starting Dose in Initial Clinical Trials for Therapeutics in Adult Healthy Volunteers, pp. 1-27 (Jul. 2005).

FDA, Approved Drug Products with Therapeutic Equivalence Evaluations, 23rd Edition (2003), 5 pages.
Atelvia (risedronate sodium delayed-release tablets) Highlights of Prescribing Information, 25 pages, revised Oct. 2010.
Notice of Opposition filed by Apotex Inc. on Apr. 26, 2011 against related European Patent No. 1753395 (22 pages).
Response to Opposition against related European Patent No. 1753395, filed by Warner Chilcott Company, LLC on Dec. 1, 2011 (5 pages).
Cassidy, M.M. et al., "Cellular Mechanism of Intestinal Permeability Alterations Produced by Chelation Depletion," J. Cell Biol., 32:685-98 (1967).
Chung, R.S.K., et al., "Effects of Chelation of Calcium on the Gastric Mucosal Barrier," Gastroenterology; 59(2):200-07 (1970).
Rosenblatt, D.E., et al., "Calcium Ethylenediaminetetraacetate (CaEDTA) Toxicity: Time- and Dose-Response Studies on Intestinal Morphology in the Rat," Experimental and Molecular Pathology, 28(2):215-26 (1978).
"Edetic Acid," Kibbe, A.H., Ed., Handbook of Pharmaceutical Excipients, Third Edition, Pharmaceutical Press and American Pharmaceutical Association, London, GB and Washington, DC, 191-4 (2000).
Complaint for Patent Infringement by Warner Chilcott Company, LLC and Warner Chilcott (US), LLC against Teva Pharmaceuticals USA, Inc. and Teva Pharmaceuticals Industries Ltd and Exhibits, filed Nov. 22, 2011 (60 pages).
Complaint for Patent Infringement by Warner Chilcott Company, LLC and Waner Chilcott (US), LLC against Watson Pharmaceuticals, Inc., Watson Laboratories, Inc.—Florida, and Watson Pharma, Inc. and Exhibits, filed Oct. 12, 2011 (65 pages).
Watson Laboratories, Inc.—Florida's Answer, Separate Defenses, and Amended Counterclaims to Plaintiffs' Complaint filed Jan. 4, 2012 (13 pages).
Russell, R.G., et al., "Bisphosphonates an Update on Mechanisms of Action and How These Relate to Clinical Efficacy," Ann. N.Y. Acad. Sci., 1117:209-257 (2007).
Nancollas, G.H., et al., "Novel Insights into Action of Bisphosphonates on Bone: Differences in Interactions with Hydroxyapatite," BONE, 38: 617-627 (2005).
Dunford, J.E., et al., "Structure-Activity Relationships for Inhibition of Farnesyl Diphosphate Synthase in Vitro and Inhibition of Bone Resorption in Vivo by Nitrogen-Containing Bisphosphonates," The Journal of Pharmacology and Experimental Therapeutics, 296(2): 235-242 (2001).
Fleisch, H. "Chemistry and Mechanisms of Action of Bisphosphonates," Bone Resorption, Metastasis, and Diphosphonates, Silvio Garattini, ed., Raven Press, New York, pp. 33-40 (1985).
Teva Pharmaceutical's Notice of Paragraph IV Certification concerning Risedronate-Sodium Delayed-Release Tablets, Oct. 13, 2011 (45 pages).
Watson Laboratories, Inc.—Florida's Notification of Certification of Invalidity and/or Non-infringement of U.S. Patent Nos. 7,645,459 and 7,645,460, Aug. 29, 2011 (37 pages).
PDR (Physicians' Desk Reference: 55th edition (2001), p. 331).
Office Action issued in related Japanese Application No. 2008-506439 and translation (Mar. 29, 2011) (7 pages).
"Actonel (risedronate sodium tablets)," label (Mar. 2003) (24 pages).
Decision revoking the European Patent issued in the Opposition of European Patent No. 1753395, dated Nov. 19, 2012.
Provision of the minutes from the oral proceeding in the Opposition of European Patent No. 1753395, dated Nov. 19, 2012.

LOW DOSAGE FORMS OF RISEDRONATE OR ITS SALTS

CROSS REFERENCE TO RELATED APPLICATION

This application is a continuation of application Ser. No. 12/183,359, filed Jul. 31, 2008, which is a continuation-in-part of application Ser. No. 11/286,875, filed Nov. 23, 2005, which is a continuation-in-part of application Ser. No. 11/106,816, filed Apr. 15, 2005, which claims the benefit of U.S. Provisional Application No. 60/573,881, May 24, 2004, all of which are incorporated by reference herein.

FIELD OF THE INVENTION

The present invention relates to oral dosage forms of risedronate comprising risedronate, a chelating agent for enabling administration of risedronate with food, and means for effecting delayed release of risedronate and the chelating agent in the small intestine. The oral dosage forms of the invention provide delivery of the pharmaceutical composition to the small intestine of the mammal subject and provide pharmaceutically effective absorption of risedronate when administered with or without food or beverages. The present invention further relates to a method of treating or preventing diseases characterized by abnormal calcium and phosphate metabolism comprising administering to a human or other mammal in need thereof the oral dosage form described herein.

BACKGROUND OF THE INVENTION

Bisphosphonates were first developed to complex calcium in hard water to improve detergent performance. Bisphosphonates have since been found to be useful in the treatment and prevention of diseases or conditions characterized by abnormal calcium and phosphate metabolism. Such conditions may be divided into two broad categories:
1. Conditions which are characterized by anomalous mobilization of calcium and phosphate leading to general or specific bone loss or excessively high calcium and phosphate levels in the fluids of the body. Such conditions are sometimes referred to herein as pathological hard tissue demineralization.
2. Conditions which cause or result from deposition of calcium and phosphate anomalously in the body. These conditions are sometimes referred to herein as pathological calcifications.

The first category includes osteoporosis, a condition in which bone hard tissue is lost disproportionately to the development of new hard tissue. Essential quantities of cancellous bone are lost, and marrow and bone spaces become larger, resulting in reduced cancellous bone strength. Bone also becomes less dense and fragile. Osteoporosis can be sub-classified as senile, drug induced (e.g., adrenocorticoid, as can occur in steroid therapy), disease induced (e.g., arthritic and tumor), etc., however the manifestations are similar. Another condition in the first category is Paget's disease (osteitis deformans). In this disease, dissolution of normal bone occurs, which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastasis are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis, and other inflammatory conditions which predispose involved tissue to deposition of calcium phosphates.

Bisphosphonates tend to inhibit the resorption of bone tissue, which is beneficial to patients suffering from excessive bone loss. However, many of the early bisphosphonates, such as ethane-1,1-diphosphonic acid (EHDP), propane-3-amino-1-hydroxy-1,1-diphosphonic acid (APD), and dichloromethane diphosphonic acid ($Cl_2MDP$), have the propensity of inhibiting bone mineralization when administered at high dosage levels. Although more biologically potent bisphosphonates exist, which can be administered at lower dosage levels (such as 1-hydroxy-2-(3-pyridinyl)-ethylidene-1,1-bisphosphonic acid (risedronate), alendronate, ibandronate, and zoledronate), oral administration of bisphosphonates sometimes results in patient complaints shortly after dosing. These complaints are usually characterized by the patients as heartburn, esophageal burning, pain and/or difficulty upon swallowing, and/or pain existing behind and/or mid-sternum. It is hypothesized that this irritation results from the bisphosphonate tablet adhering to epithelial and mucosal tissues, resulting in the topical irritation thereof. In order to avoid potential upper gastrointestinal irritation, patients taking bisphosphonates are instructed to take their medication with a full glass of water, and to remain upright for at least thirty minutes after taking an oral dose of a bisphosphonate.

It is known that oral doses of bisphosphonates are poorly absorbed (less than 1% of the oral dose) in the gastrointestinal (GI) tract. See Ezra et al., Adv. Drug Del. Rev. 42: 175-95 (2000). Several approaches have been suggested for increasing absorption of oral bisphosphonates throughout the GI tract. These approaches include modifying the permeability properties of the intestinal mucosa (e.g., through the use of absorption enhancers), or altering the physical or chemical properties of the bisphosphonate compounds themselves (e.g., through prodrugs).

While the use of absorption enhancers, such as ethylenediaminetetraacetic acid (EDTA), that increase intestinal permeability at high doses, has been proposed as a means of increasing absorption of oral bisphosphonates, the applicability of EDTA as an agent in human pharmacotherapy has been thought to be "impossible" in light of the effects of EDTA on mucosal integrity. Ezra et al., Adv. Drug Del. Rev. 42: 185 (2000). Still others have concluded that the high amount of EDTA required to effect an increase in GI absorption would exclude the agent as a candidate for use in oral bisphosphonate therapies. See Janner et al., Calcif. Tissue Int. 49: 280-83 (1991).

While the primary site of bisphosphonate absorption is the small intestine, bisphosphonates such as risedronate have similar absorption throughout the small intestine independent of where it was delivered. See Mitchell et al., Pharm Res., Vol. 15, No. 2: 228-232 (1998). Thus targeted delivery of the bisphosphonate alone to the small intestine would not increase absorption or efficacy of the bisphosphonate. However, others have attempted to increase the absorption of bisphosphonates by increasing the permeability of the intestinal mucosa through delivery of microparticles of chelating agents and bisphosphonate to the reported site of absorption (BR2001-006601).

Bisphosphonates such as risedronate and alendronate have been approved by a number of regulatory agencies as being effective in the treatment of various bone pathologies. However, interactions between bisphosphonates and foods and minerals (especially cations like calcium, magnesium, aluminum, and iron-containing foods or supplements) cause less of the bisphosphonate to be available for absorption. For example, in Mitchell et. al., Br. J. Clin. Pharmacol. 48: 536-542 (1999), it was demonstrated that administration of risedronate within 30 minutes of a meal reduced the amount absorbed by 50% compared to administration in the fasting state. In order to reduce this food effect, the labeling of oral bisphosphonate products instruct patients to take their medication at least thirty minutes or in the case of ibandronate sixty minutes, before the first food of the day, and are instructed to take their calcium supplements at another time of the day, or on a day when they are not taking an oral dose of a bisphosphonate. These dosing instructions can seem complex and inconvenient to the patient, which can lead to poor patient compliance.

There is an ongoing need to develop an oral dosage form of a bisphosphonate which can be taken with or without food or beverages (i.e., has pharmaceutically effective absorption regardless of food or beverage intake), at the preference of the patient, and which does not produce upper gastrointestinal irritation.

It has been found that an oral dosage form comprising risedronate, a sufficient amount of chelating agent to bind the ions and minerals in food, and a means for effecting delayed release of risedronate and the chelating agent in the small intestine is useful in providing immediate release of risedronate to the small intestine, as well as pharmaceutically effective absorption of risedronate when administered with or without food or beverages. The oral dosage forms of the present invention may be taken with or without food or beverages, thus simplifying the bisphosphonate treatment therapy and leading to increased patient compliance and convenience. Substantial reduction in the food effect using the present invention may not only allow the new formulation to be taken with or without food, but also achieve the same clinical benefit at a lower dose relative to known products. Further, the oral dosage forms of the invention provide for delayed release of risedronate and the chelating agent in the small intestine, which may alleviate the upper gastrointestinal irritation experienced with other oral bisphosphonate dosage forms and the need to remain upright for thirty minutes post-dose administration.

SUMMARY OF THE INVENTION

The present invention relates to an oral dosage form comprising:
(a) from about 50 mg to less than 150 mg of a bisphosphonate selected from the group consisting of risedronate and salts thereof;
(b) from about 10 mg to about 1000 mg of a chelating agent; and
(c) a delayed release mechanism to immediately release the risedronate and the chelating agent in the small intestine.

The dosage forms of the present invention provide an immediate release of risedronate and the chelating agent to the small intestine of the mammal subject and pharmaceutically effective absorption of risedronate active ingredient when administered with or without food or beverages.

The present invention substantially alleviates the interaction between risedronate and food, which interaction results in decreased absorption of risedronate. The resulting novel oral dosage form may thus be taken with or without food or beverages, which simplifies previously complex treatment regimens and can lead to increased patient compliance with bisphosphonate therapies and if the patients are compliant their disease can be better treated. The invention further alleviates the potential for upper gastrointestinal irritation associated with immediate release oral dosage forms of bisphosphonates, by delaying release of the bisphosphonate active ingredient until the bisphosphonate and the chelating agent reach the small intestine.

The present invention further relates to a method of treating or preventing diseases characterized by abnormal calcium and phosphate metabolism comprising administering to a human or other mammal in need thereof the oral dosage form described herein.

The oral dosage form may be continuously administered on a monthly basis, i.e., once every thirty days or once every calendar month.

The invention further relates to a kit comprising one or more oral dosage forms of the present invention and means for facilitating compliance with methods of this invention.

DETAILED DESCRIPTION OF THE INVENTION

The term "immediate release" as used herein means dissolution of the core tablet in less than 60 minutes, when measured by standard USP definitions. For example, the USP specifies that all tablets and capsules are subject, to a general dissolution standard of not less than 75% of the core content is dissolved in not more than 45 minutes in 900 mL of water, using the apparatus, procedures, and interpretation presented in the United States Pharmacopeia chapter, Dissolution, page 959. For this purpose, 75% is Q, and conformance is demonstrated with either one of Apparatus 1 at 100 rpm or Apparatus 2 at 50 rpm."

The terms "continuous" or "continuously," as used herein, mean at regular specified intervals. For example, a continuous schedule according to a dosing regimen of once monthly means that the active is given one time per every thirty days or one time per calendar month for an unspecified period of time or for as long as treatment is necessary.

The term "delayed release or delayed delivery," as used herein, refers to formulating the pharmaceutical composition comprising risedronate and the chelating agent so that their release will be accomplished at some generally predictable location in the small intestine more distal to that which would have been accomplished had there been no alteration in the delivery of the risedronate and the chelating agent.

The term "nutrient," as used herein, means any nutritional or dietary supplement including but not limited to vitamins, minerals, amino acids, herbs or other botanicals, or concentrates, metabolites, constituents, extracts, or combinations of the same.

The term "pharmaceutical composition," as used herein, means an oral dosage form comprised of a safe and effective amount of risedronate and one or more pharmaceutically-acceptable excipients including at least one chelating agent. The pharmaceutical compositions described herein are comprised of from 0.5% to 75%, preferably from 1% to 40% of risedronate and from 25% to 99.5%, preferably from 60% to 99% of pharmaceutically-acceptable excipients including at least one chelating agent.

The term "safe and effective amount," as used herein, means an amount of a compound or composition high enough to significantly positively modify the symptoms and/or condition to be treated, but low enough to avoid serious side effects (at a reasonable risk/benefit ratio), within the scope of sound medical judgment. The safe and effective amount of active ingredient for use in the method of the invention herein will vary with the particular condition being treated, the age and physical condition of the patient to be treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically effective absorption" as used herein means an amount of a chelating compound high enough to significantly bind the metal ions and minerals in food but low enough not to significantly alter absorption of risedronate as compared to absorption in the fasted state. That is, absorption is similar with or without food. Given the high variability of bisphosphonate absorption, fed exposure within about 50% of fasting exposure is expected to be pharmaceutically effective absorption.

The term "oral dosage form," as used herein, means any pharmaceutical composition intended to be delivered or released to the small intestine of a human or other mammal via the mouth of said human or other mammal.

The term "unit dose" or "unit dosage" means a dosage form containing an amount of pharmaceutical active or nutrient suitable for administration in one single dose, according to sound medical practice. The present invention is particularly useful for the administration of unit doses in the form of tablets and capsules.

The term "gastrointestinal tract" or "GI tract," as used herein, relates to the alimentary canal, i.e., the musculo-membranous tube about thirty feet in length, extending from the mouth to the anus. The term "upper gastrointestinal tract," as used herein, means the buccal cavity, the pharynx, the esophagus, and the stomach. The term "lower gastrointestinal tract," as used herein, means the small intestine and the large intestine.

The term "small intestine," as used herein, means the part of the small intestine consisting of just distal to the stomach (the duodenum, the jejunum, and the ileum), i.e., that portion of the intestinal tract just distal to the duodenal sphincter of the fundus of the stomach and proximal to the large intestine. The term "large intestine," as used herein, means the part of the lower gastrointestinal tract including the ascending colon, the transverse colon, the descending colon, the sigmoid colon, and the rectum Risedronate The terms "bisphosphonate" and "diphosphonate," as used herein, include acids, salts, esters, hydrates, polymorphs, hemihydrates, solvates, and derivatives thereof. The bisphosphonates of the present invention include those forms of 1-hydroxy-2-(3-pyridinyl)-ethylidene-1,1-bisphosphonic acid (risedronate) as described in U.S. Pat. No. 5,583,122, to Benedict et al., issued Dec. 10, 1996; U.S. Pat. No. 6,410,520 B2, to Cazer et al., issued Jun. 25, 2002

Non-limiting examples of salts useful herein include those selected from the group consisting of alkali metal, alkaline metal, ammonium, and mono-, di-, tri-, or tetra-$C_1$-$C_{30}$-alkyl-substituted ammonium. Preferred salts are those selected from the group consisting of sodium, potassium, and ammonium salts.

Mixed nomenclature is currently in use by those of ordinary skill in the art, for example reference to a specific weight or percentage of a bisphosphonate active ingredient is on an anhydrous monosodium salt basis for risedronate. As an example, the phrase "about 100 mg of risedronate, pharmaceutically acceptable salts thereof, and mixtures thereof, on an anhydrous monosodium salt basis" means that the amount of the risedronate compound selected is calculated based on about 100 mg of anhydrous risedronate monosodium salt.

As is discovered herein, substantial reduction in the food effect using the present invention may not only allow the new formulation to be taken with or without food, but also achieve the same clinical benefit at a lower dose relative to known products. The oral dosage form contains from about 50 mg to less than 150 mg of the risedronate, alternatively from about 75 to about 125 mg of the risedronate, and alternatively about 100 mg of the risedronate (all on a risedronate anhydrous monosodium salt basis).

Chelating Agent

The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom. See Kirk-Othmer Encyclopedia of Chemical Technology (4th ed. 2001).

In homogeneous dilute solutions, the equilibrium constant for the formation of the complex from the solvated metal ion (e.g., calcium) and the chelating agent in its fully dissociated form is called the formation or stability constant, K. The practical significance of formation constants is that a high log K value means a large ratio of chelated to unchelated (or free) metal ion, when equivalent amounts of metal ion and chelating agent are present. Higher ratios (or difference if K is expressed in log units) of the chelating agent and the bisphosphonate complexation constants are preferred in order to have nearly all of the metal ion complexed to the chelating agent instead of the bisphosphonate. For example, for equal molar amounts of both bisphosphonate and the chelating agent, in order for the metal ions to be 99% complexed to the chelating agent, the chelating agent must have a log K which is at least 4 units higher than the bisphosphonate-metal ion complex. The other technique which can be used to favor the chelating agent-metal ion complex over that of the bisphosphonate-metal ion complex is to add a molar excess of the chelating agent which relies on the law of mass action to favor formation of the chelating agent-metal ion complex.

Although pH and solution concentration can affect the formation constant, in general, the log K of the chelating agent is preferably at least equal to that of the bisphosphonate. In other instances the log K of the chelating agent is 2 to 5 units higher than that of the bisphosphonate. In other instances, the chelating agent is present at a molar excess to that of the bisphosphonate. The chelating agent in such instances is present in at least a 2:1 molar ratio of the chelating agent to bisphosphonate.

In one embodiment, the chelating agent is selected from the group consisting of sodium or disodium EDTA, citric acid, malic acid, tartaric acid, lactic acid, adipic acid, succinic acid, lysine, sodium hexametaphosphate, and combinations thereof. In another embodiment, the chelating agent is sodium or disodium EDTA, citric acid, or sodium hexametaphosphate.

The amount of chelating agent present in the oral dosage form of the present invention will depend on the particular chelating agent or agents (i.e., mixtures of chelating agents) selected, the amount of bisphosphonate active ingredient present in the oral dosage form, and the specific portion of the small intestine where delivery and release of the chelating agent and/or bisphosphonate active ingredient is desired. After the ingestion of milk, it has been shown in the art that the concentration of calcium decreases over the length of the lower GI tract, beginning with the small intestine and proceeding through to the end of the small intestine. Mahe, J. et al., *Gastroileal nitrogen and electrolyte movements after bovine milk ingestion in humans*, Am. J. Clin. Nutr. 56: 410-16 (1992).

The concentration of calcium in the stomach is approximately 10-fold higher than that of the concentration in the jejunum and approximately 40 times that in the ileum. Thus if the risedronate and chelating agent were released in the stomach (with food), the amount of chelating agent would be insufficient to overcome the effect of calcium on drug absorption. The concentration of calcium in the jejunum and ileum are lower and by targeting release of the dosage form in these regions where the amount of calcium is lower, the chelating agent is more effective at binding most or all of the calcium than if released in the stomach. It is also desirable to target release of the tablet in the small intestine and after the coating dissolves and releases the chelating agent and risedronate from the core tablet in an immediate release fashion. This will maximize the local concentration of the chelant in relationship to that of the calcium in the small intestine. Slow or prolonged delivery of the chelating agent in the small intestine is not anticipated to achieve the desired local concentration of the chelating agent and this type of delivery will not overcome the food effect.

Generally, the oral dosage forms of the present invention will contain a safe and effective amount of a chelating agent suitable for achieving the desired chelating effect, that is, chelating the residual metal ions that are present in the gastrointestinal tract from food at the site of delivery without significantly affecting the absorption of the bisphosphonate had no food been present. In one embodiment, the oral dosage form contains from about 10 mg to about 1000 mg of a chelating agent. In another embodiment, the oral dosage forms contain from about 10 mg to about 500 mg of a chelating agent. When the chelating agent is disodium EDTA, an optional range is from about 55 mg to about 500 mg, alternatively from about 75 mg to about 250 mg, alternatively from about 75 mg to about 150 mg, alternatively about 100 mg. When the chelating agent is citric acid, an optional range is from about 100 mg to about 970 mg, alternatively from about 250 mg to about 500 mg per unit dose.

Delayed Delivery to the Small Intestine

The ultimate site of and/or the rate of delivery in the small intestine can be satisfactorily controlled by one skilled in the art, by manipulating any one or more of the following:
(a) the active ingredient proper;
(b) the type and level of disintegrant;
(c) the type of coating, the type and level of excipients added to the coating and the concomitant desirable thickness and permeability (swelling properties) of the coating;
(d) the time dependent conditions of the coating itself and/or within the coated tablet, particle, bead, or granule;
(e) the particle size of the granulated active ingredient;
(f) the pH dependent conditions of the coating itself and/or within the coated tablet, particle, bead, or granule;
(g) the particle size or solubility of the chelating agent;
(h) the dissolution rate of the coating;
(j) size or shape of the tablet.

In addition the pharmacodynamic effect of the tablets, after multiple dosing, should be within at least 75% of the comparable immediate release tablet.

Delayed Release in the Small Intestine

A human or other mammal suffering from diseases or disorders involving calcium and phosphate metabolism can be successfully treated by the delivery of risedronate to the small intestine of said human or other mammal. The novel dosage forms described herein effect an immediate release to the small intestine, and prohibit the undesired release of risedronate in the mouth, pharynx, esophagus, and/or stomach, thereby prohibiting the erosion, ulceration, or other like irritation of the epithelial or mucosal layers of these tissues.

The chelant and risedronate are released rapidly and as close to simultaneously as possible. This causes the local concentration of chelating agent to be higher in relationship to the metal ions in the food. The higher local concentration of chelating agent in the environment where the active is released may more effectively complex the metals in the food and facilitate absorption of the bisphosphonate. This can be conveniently achieved from a single tablet.

Various means for targeting release of risedronate and the chelating agent in the small intestine are suitable for use in the present invention. Non-limiting examples of means for delivery to the small intestine include pH triggered delivery systems and time dependent delivery systems.

pH Triggered Delivery Systems

One embodiment of the present invention involves coating (or otherwise encapsulating) the risedronate and the chelating agent(s) with a substance which is not broken down, by the gastrointestinal fluids to release the risedronate and the chelating agent until a specific desired point in the intestinal tract is reached. In one embodiment, delayed release of the pharmaceutical composition is achieved by coating the tablet, capsule, particles, or granules, of the risedronate and the chelating agent with a substance which is pH dependent, i.e., broken down or dissolves at a pH which is generally present in the small intestine, but not present in the upper GI tract (i.e., the mouth, buccal cavity, pharynx, esophagus, or stomach) or lower GI tract.

In some cases, it may be desirable that the risedronate and the chelating agent are released at a particular location in the small intestine. In other cases, it may be desirable to release the risedronate and the chelating agent independently at different locations within the small intestine. For example, it may be desirable to release the chelating agent in the, jenunum and the risedronate in the ileum. When targeted release of the risedronate and the chelating agent together or separately in particular locations within the small intestine is desired, the selection of the coating material and/or the method of coating or otherwise combining the risedronate and the chelating agent with the selected coating material or other pharmaceutically-acceptable excipients may be varied or altered as is described herein, or by any method known to one skilled in the art.

Solubility, acidity, and susceptibility to hydrolysis of the different risedronate active ingredients, such as acid addition salts, salts formed with the phosphonic group (e.g., alkali metal salts, alkaline earth metal salts, etc.), and esters (e.g., alkyl, alkenyl, aryl, arylalkyl) may be used as guidelines for the proper choice of coating. In addition, suitable pH conditions might be established within the coated tablets, particles, or granules by adding a suitable buffer to the active ingredient in accordance with the desired release pattern.

One embodiment of the present invention is delivered to the small intestine utilizing a pH dependent enteric coating material made from a partly methyl esterified methacrylic acid polymer. The oral dosage form can be in the form of an enteric coated compressed tablet made of granules or particles of active ingredient.

Any enteric coating which is insoluble at a pH below 5.5 (i.e., that generally found in the mouth, pharynx, esophagus, and stomach), but soluble between about pH 5.5 and about pH 6.5 (i.e., that present in the small intestine) can be used in the practice of the present invention. Accordingly, when it is desired to effect delivery of the bisphosphonate and the chelating agent to the small intestine, any enteric coating is suitable which is wholly- or partially-insoluble at a pH below 5.5 and soluble at about a pH 5.5 to about pH 6.5.

The enteric coating must be applied to the compressed tablet, or capsule (e.g., gelatin, starch, or hydroxypropylmethylcellulose) in a sufficient thickness so that the entire coating does not dissolve in gastrointestinal fluids at a pH below 5.5, but does dissolve at a pH above about 5.5 and below pH about 6.5 The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present invention to achieve delivery of the bisphosphonate and chelating agent to the small intestine. The coating chosen must be compatible with the particular risedronate active ingredient selected. The preferred polymers for use in the present invention are anionic carboxylic polymers. It is particularly preferred that the polymers are acrylic polymers, more preferably partly methyl-esterified methacrylic acid polymers, in which the ratio of free anionic carboxyl groups to ester groups is about 1:1.

A particularly suitable methacrylic acid copolymer is Eudragit L®, particularly Eudragit L 30 D-55® and Eudragit L 100-55®, manufactured by Röhm Pharma GmbH and Co. KG, Darmstadt, Germany. In Eudragit L 30 D-55®, the ratio of free carboxyl groups to ester groups is approximately 1:1. Further, said copolymer is known to be insoluble in GI fluids having a pH below 5.5, generally 1.5-5.5, i.e., that generally present in the fluid of the upper GI tract, but readily soluble at pH above 5.5, i.e., that generally present in the fluid of the small intestine.

The coating can, and usually will, contain a plasticizer and possibly other coating excipients such as coloring agents, surfactant, talc, and/or magnesium stearate, many of which are well known in the coating art. In particular, anionic carboxylic acrylic polymers usually will contain 10-25% by weight of a plasticizer, especially triethyl citrate, tributyl citrate, acteyltriethyl citrate, dibutyl phthalate, diethyl phthalate, polyethylene glycol, acetylated monoglycerides propylene glycol, and triacetin. Conventional coating techniques such as fluid-bed or pan coating are employed to apply the coating. Coating thickness must be sufficient to ensure that the oral dosage form remains essentially intact until the desired site of delivery in the small intestine is reached.

The solid oral dosage form may be in the form of a coated compressed tablet which contains particles or granules of the bisphosphonate active ingredient and the chelating agent, or of a soft or hard capsule (e.g., gelatin, starch, or hydroxypropylmethylcellulose), coated or uncoated, which contains beads or particles of the bisphosphonate active ingredient and the chelating agent, which themselves are enterically coated. In an embodiment of the invention the tablets are compressed and the tablet is enteric coated.

Suitable enteric coating materials include Eudragit L-100®, Eudragit L 30 D-55®, cellulose acetate phthalate, shellac, or any enteric coating material that dissolves at about pH 5.5 to about 6.5. The enteric coating is applied using various spray techniques known to one skilled in the art. The enteric coating may further comprise one or more pharmaceutically-acceptable excipients including, but not limited to, talc, triethyl citrate, polyethylene glycol, Tween 80® (polyoxyethylene sorbitan monooleate, available from Sigma Chemical CO., St. Louis, Mo.), castor oil. The enteric coating is applied to the tablet core to provide a weight gain of 2.5% to 40%.

The tablet core comprises a bisphosphonate active ingredient, a chelating agent, and may contain one or more pharmaceutically-acceptable excipients. Suitable excipients include, but are not limited to, crystalline cellulose, lactose, calcium hydrogen phosphate, polyvinylpyrrolidone, magnesium stearate, sucrose, starch, magnesium oxide, sodium starch glycolate and sodium lauryl sulfate.

Time Dependent Delivery Systems

In another embodiment of the invention, delivery of the risedronate and the chelating agent to the small intestine is achieved through the use of a time dependent delivery system. Given established transit times after gastric emptying, drug and/or chelating agent release can be targeted to the various segments of the small intestine. Approaches to time dependent delivery systems suitable for use in the present invention include, but are not limited to, such devices as the Pulsincap™ (Scherer DDS, Strathclyde, U.K.), the Time Clock™ (Zambon Group, Milan, Italy), and SyncroDose™ (Penwest, Patterson, N.Y.), as well as various coatings which degrade over time to release tablet contents such as hydroxypropylmethylcellulose, hydroxypropylcellulose, or any suitable hydrogel.

In one embodiment of the invention, the time-dependent device Pulsincap™ is used to target delivery of the active ingredient and the chelating agent to the small intestine. The active ingredient and other excipients, including the chelating agent, are contained inside the Pulsincap™ water-insoluble capsule by means of a hydrogel plug which is covered by a water-soluble cap. The entire dose form is optionally coated in an enteric-coating material to protect the dose form from degradation while in transit through the upper GI tract. When the patient swallows the Pulsincap™ dosage form, the water-soluble cap dissolves and exposes the hydrogel plug to gastric and/or intestinal fluids. The hydrogel cap then swells, and eventually pops out of the capsule body, thus releasing the capsule contents. Release of the capsule contents can be targeted to specific regions of the small intestine by modifying the hydrogel plug properties. Watts, Peter J. & Illum, Lisbeth, Drug Dev. and Indus. Pharm., 23(9): 893-917 (1997).

In one embodiment of the invention, a time dependent coating is applied over a compressed tablet and then an enteric coating is applied over the time dependent coating. This is used to target delivery of the active ingredient and the chelating agent to the small intestine. The active ingredient and other excipients, including the chelating agent, are contained inside the core tablet. The entire dose form is coated with a time dependent coating and then an enteric coating. The enteric-coating material is to protect the dose form from degradation while in transit through the upper GI tract. When the patient swallows the dosage form the enteric coating dissolves after the dosage form leaves the stomach and then the core tablet starts to swell. Eventually, at a predetermined time in the small intestine fluids, the time dependent coating will rupture and releases the contents of the core tablet in the small intestine. Release of the core tablet contents can be targeted to specific regions of the small intestine by modifying the core tablet, time dependent coating and/or the enteric coating.

Pharmaceutically-Acceptable Excipients

Pharmaceutically-acceptable excipients include, but are not limited to, polymers, resins, plasticizers, fillers, lubricants, diluents, binders, disintegrants, solvents, co-solvents, surfactants, buffer systems, preservatives, sweetener agents, flavoring agents, pharmaceutical-grade dyes or pigments, chelating agents, viscosity agents, and combinations thereof. Pharmaceutically-acceptable excipients can be used in any component in making the oral dosage form, i.e. core tablet or coating.

Flavoring agents and dyes and pigments among those useful herein include but are not limited to those described in Handbook of Pharmaceutical Excipients (4th Ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, simethicone emulsion, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, (Röhm Pharma GmbH and Co. KG, Darmstadt, Germany), and Acryl-EZE® and Sureteric® (Colorcon, Inc., West Point, Pa.).

Suitable lubricants include, but are not limited to, magnesium stearate, stearic acid, and talc.

Methods of Use

The present invention further relates to a method of treating or preventing diseases characterized by abnormal calcium and phosphate metabolism comprising administering to a human or other mammal in need thereof a safe and effective amount of a pharmaceutical composition delivered to said human or other mammal via the oral dosage forms described herein.

Diseases characterized by abnormal calcium and phosphate metabolism include, but are not limited to, osteoporosis, Paget's disease (osteitis deformans), hyperparathyroidism, hypercalcemia of malignancy, osteolytic bone metastasis, myositis ossificans progressiva, calcinosis universalis, and such afflictions as arthritis, neuritis, bursitis, tendonitis, and other inflammatory conditions which predispose involved tissue to deposition of calcium phosphates.

The oral dosage forms of the present invention are suitable for administration to a patient according to a continuous monthly dosing interval.

Kits

The present invention further comprises kits that are particularly useful for administering the oral dosage forms described herein according to a monthly continuous dosing schedule. Such kits comprise one or more oral dosage forms comprising risedronate (or salt) and a chelating agent and a means for facilitating compliance with methods of this invention. Such kits provide a convenient and effective means for assuring that the subject to be treated takes the appropriate oral dosage form in the correct dosage and in the correct manner. The compliance means of such kits includes any means which facilitates administering the active according to a method of this invention. Such compliance means includes instructions, packaging, and dispensing means, and combinations thereof. The kits can also comprise a means for aiding the memory, including but not limited to a listing of the days of the week, numbering, illustrations, arrows, Braille, calendar stickers, reminder cards, or other means specifically selected by the patient. Examples of packaging and dispensing means are well known in the art, including those described in U.S. Pat. No. 4,761,406, Flora et al., issued Aug. 2, 1988; and U.S. Pat. No. 4,812,311, Uchtman, issued Mar. 14, 1989.

Optionally, the kits can comprise at least one oral dosage form comprising a risedronate and a chelating agent and at least one oral dosage form of an accompanying nutrient. Preferred nutrients are calcium and/or vitamin D. Oral forms of calcium suitable for use in the present invention include capsules, compressed tablets, chewable tablets, and the like. Typical salt forms of calcium suitable for use in the present invention include but are not limited to calcium carbonate, calcium citrate, calcium malate, calcium citrate malate, calcium glubionate, calcium gluceptate, calcium gluconate, calcium lactate, dibasic calcium phosphate, and tribasic calcium phosphate. In one embodiment, kits of the present invention may include tablets comprising 400 mg to 1500 mg calcium.

The term "vitamin D," as used herein, refers to any form of vitamin D that may be administered to a mammal as a nutrient. Vitamin D is metabolized in the body to provide what is often referred to as "activated" forms of vitamin D. The term "vitamin D" can include activated and non-activated forms of vitamin D, as well as precursors and metabolites of such forms. Precursors of these activated forms include vitamin $D_2$ (ergocalciferol, produced in plants) and vitamin $D_3$ (cholecalciferol, produced in skin and found in animal sources and used to fortify foods). Vitamins $D_2$ and $D_3$ have similar biological efficacy in humans. Non-activated metabolites of vitamins $D_2$ and $D_3$ include hydroxylated forms of vitamins $D_2$ and $D_3$. Activated vitamin D analogs cannot be administered in large doses on an intermittent schedule, due to their toxicity in mammals. However, non-activated vitamin $D_2$, vitamin $D_3$, and their metabolites may be administered in larger doses than "active" forms of vitamin D on an intermittent basis, without toxicity. In one embodiment, kits of the present invention may include tablets comprising 100 IU to 10,000 IU of vitamin D.

In another embodiment, kits of the present invention may include one or more nutrient tablets comprising both calcium and vitamin D. In a further embodiment, the unit dose of nutrient comprises about 600 mg calcium and about 400 IU vitamin D.

The following non-limiting examples illustrate the formulations, processes, and uses of the present invention.

EXAMPLES

Example I

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
|---|---|
| Eudragit L 30 D-55 ® (wet basis) (manufactured by Röhm Pharma GmbH and Co. KG, Darmstadt, Germany) | 73.65 mg |
| Triethylcitrate | 2.21 mg |
| Talc | 16.57 mg |
| Yellow Iron Oxide | 0.03 mg |
| Simethicone | 0.07 mg |
| Polysorbate 80 | 0.22 mg |
| Purified Water | 113.2 mg |

The enteric coating is prepared using the following method:

A pigment suspension is prepared by adding polysorbate 80, ground ferric oxide, and talc to approximately three-quarters of the purified water while mixing. The suspension is mixed for at least 60 minutes. The simethicone and the remaining water are added to the pigment suspension and mixed for at least 60 minutes. The Eudragit L 30 D-55 is screened then combined with triethyl citrate and mixed for at least 45 minutes. The pigment suspension is then added to the Eudragit solution and mixed for 30 to 60 minutes. The resulting coating suspension is mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 10% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 75 mg risedronate tablets, each tablet weighing 390 mg and each containing:

| Active Ingredients: | |
|---|---|
| Risedronate Sodium | 75 mg* |
| Chelant: | |
| Disodium EDTA | 100 mg |
| Excipients | |
| Prosolv SMCC 90 | 181.8 mg |
| Sodium starch glycolate | 9.7 mg |
| Stearic acid | 19.5 mg |
| Magnesium stearate | 3.9 mg |

*This amount is calculated on a risedronate anhydrous monosodium salt basis.

Tablets having the composition set forth above are prepared as follows:

Pass the edetate disodium, risedronate sodium, and ProSolv SMCC 90 through a mill and transfer to a blender equipped with an intensifier bar. Blend with intensifier bar on for 10 minutes. Pass the sodium starch glycolate through a mill and add to the blender. Blend for 8 minutes with the intensifier bar off. The stearic acid and magnesium stearate are screened and added to the blender. The blend is mixed for approximately 3 minutes with the intensifier bar off. The blend is compressed into tablets using a suitable tablet press.

Example II

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
|---|---|
| Eudragit L 30 D-55 ® (wet basis) (manufactured by Röhm Pharma GmbH and Co. KG, Darmstadt, Germany) | 77.34 mg |
| Triethylcitrate | 2.32 mg |
| Talc | 17.4 mg |
| Yellow Iron Oxide | 0.03 mg |
| Simethicone | 0.07 mg |
| Polysorbate 80 | 0.23 mg |
| Purified Water | 118.88 mg |

The enteric coating is prepared using the following method:

A pigment suspension is prepared by adding polysorbate 80, ground ferric oxide, and talc to approximately three-quarters of the purified water while mixing. The suspension is mixed for at least 60 minutes. The simethicone and the remaining water are added to the pigment suspension and mixed for at least 60 minutes. The Eudragit L 30 D-55 is screened then combined with triethyl citrate and mixed for at least 45 minutes. The pigment suspension is then added to the Eudragit solution and mixed for 30 to 60 minutes. The resulting coating suspension is mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 10% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 100 mg risedronate tablets, each tablet weighing 440 mg and each containing:

| Active Ingredients: | |
|---|---|
| Risedronate Sodium | 100 mg* |
| Chelant: | |
| Disodium EDTA | 100 mg |
| Excipients | |
| Prosolv SMCC 90 | 202.6 mg |
| Sodium starch glycolate | 11 mg |
| Stearic acid | 22 mg |
| Magnesium stearate | 4.4 mg |

*This amount is calculated on a risedronate anhydrous monosodium salt basis.

Tablets having the composition set forth above are prepared as follows:

Pass the edetate disodium, risedronate sodium, and ProSolv SMCC 90 through a mill and transfer to a blender equipped with an intensifier bar. Blend with intensifier bar on for 10 minutes. Pass the sodium starch glycolate through a mill and add to the blender. Blend for 8 minutes with the intensifier bar off. The stearic acid and magnesium stearate are screened and added to the blender. The blend is mixed for approximately 3 minutes with the intensifier bar off. The blend is compressed into tablets using a suitable tablet press.

Example III

Enteric-Coated Tablets Containing Risedronate and EDTA

Enteric-coated tablets containing risedronate and EDTA are made by preparing a coating composition and compressed tablets containing risedronate and EDTA, and then applying said coating composition to said tablets.

An enteric coating composition is prepared in the form of a lacquer containing the following excipients, per tablet:

A. Enteric Coating Suspension

| Ingredients: | |
|---|---|
| Eudragit L 30 D-55 ® (wet basis) (manufactured by Röhm Pharma GmbH and Co. KG, Darmstadt, Germany) | 77.34 mg |
| Triethylcitrate | 2.32 mg |
| Talc | 17.4 mg |
| Yellow Iron Oxide | 0.03 mg |
| Simethicone | 0.07 mg |
| Polysorbate 80 | 0.23 mg |
| Purified Water | 118.88 mg |

The enteric coating is prepared using the following method:

A pigment suspension is prepared by adding polysorbate 80, ground ferric oxide, and talc to approximately three-quarters of the purified water while mixing. The suspension is mixed for at least 60 minutes. The simethicone and the remaining water are added to the pigment suspension and mixed for at least 60 minutes. The Eudragit L 30 D-55 is screened then combined with triethyl citrate and mixed for at least 45 minutes. The pigment suspension is then added to the Eudragit solution and mixed for 30 to 60 minutes. The resulting coating suspension is mixed throughout the coating process. The core tablets are transferred to the coating pan and preheated with occasional jogging. Tablets are coated, using a typical pan coating process until the required quantity of coating solution has been applied. Tablets are then cooled and collected in suitable containers.

A coating weight gain of 10% (total solids) is applied by spraying the above composition onto compressed tablets containing risedronate and EDTA, prepared in Part B below.

B. Compressed Tablets Containing Risedronate and EDTA

The enteric coating suspension prepared in Part A above is sprayed onto 125 mg risedronate tablets, each tablet weighing 495 mg and each containing:

| Active Ingredients: | |
|---|---|
| Risedronate Sodium | 125 mg* |
| Chelant: | |
| Disodium EDTA | 100 mg |

| Excipients | |
|---|---|
| Prosolv SMCC 90 | 227.9 mg |
| Sodium starch glycolate | 12.35 mg |
| Stearic acid | 24.75 mg |
| Magnesium stearate | 4.95 mg |

*This amount is calculated on a risedronate anhydrous monosodium salt basis.

Tablets having the composition set forth above are prepared as follows:

The risedronate sodium, edetate disodium, sodium starch glycolate, and ProSolv SMCC 90 are passed through a mill and added to a blender equipped with an intensifier bar. The mixture is blended for approximately ten minutes with the intensifier bar on. The stearic acid and magnesium stearate are screened and added to the blender. The blend is mixed for approximately 3 minutes with the intensifier bar off. The blend is compressed into tablets using a suitable tablet press.

Example IV

A 65 kg woman diagnosed with postmenopausal osteoporosis is prescribed the enteric-coated oral dosage form of Example I, to be taken once monthly.

Example V

A 70 kg man diagnosed with prostate cancer and high bone turnover is prescribed the enteric-coated oral dosage form of Example II, to be taken once monthly. The patient takes the oral dosage form once per month, immediately before going to sleep. The patient does not experience upper GI irritation or discomfort.

Example VI

A group of women diagnosed with postmenopausal osteoporosis are prescribed the enteric-coated oral dosage form of Example III, to be taken once monthly, comprising 100 mg risedronate sodium. The patients take the oral dosage form with breakfast once per month.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral dosage form comprising:
    (a) from about 50 mg to about 125 mg of a bisphosphonate selected from the group consisting of risedronate and salts thereof;
    (b) from about 10 mg to about 1000 mg of ethylenediaminetetraacetate (EDTA) or a pharmaceutically acceptable salt thereof; and
    (c) a delayed release mechanism to immediately release the bisphosphonate and the EDTA or pharmaceutically acceptable salt thereof in the small intestine.

2. The oral dosage form of claim 1 wherein the bisphosphonate is risedronate sodium.

3. The oral dosage form of claim 2 wherein the EDTA is disodium EDTA.

4. The oral dosage form of claim 2 wherein the delayed release mechanism is selected from the group consisting of pH triggered delivery systems, time dependent delivery systems and mixtures thereof.

5. The oral dosage form of claim 4 wherein the delayed release mechanism is a pH triggered delivery system.

6. The oral dosage form of claim 5 wherein the pH triggered delivery system comprises an enteric coating.

7. The oral dosage form of claim 6 wherein the enteric coating comprises methacrylic acid copolymer.

8. The oral dosage form of claim 7 comprising from about 55 mg to about 500 mg of the disodium EDTA.

9. The oral dosage form of claim 8 comprising from about 75 mg to about 250 mg of the disodium EDTA.

10. The oral dosage form of claim 9 comprising about 100 mg of the risedronate sodium.

11. The oral dosage form of claim 9 wherein the delayed release mechanism comprises a methacrylic acid copolymer.

12. The oral dosage form of claim 11 comprising about 100 mg of the risedronate sodium.

13. The oral dosage form of claim 12 comprising about 100 mg of the disodium EDTA.

14. The oral dosage form of claim 9 comprising about 75 mg of the risedronate sodium.

15. The oral dosage form of claim 11 comprising about 75 mg of the risedronate sodium.

16. The oral dosage form of claim 15 comprising about 100 mg of disodium EDTA.

17. The oral dosage form of claim 16, wherein the methacrylic acid copolymer is poly (methacylic acid, ethyl acrylate) 1:1.

18. The oral dosage form of any one of claims 6, 7, 11, 13 and 14 to 17, wherein the enteric coating does not entirely dissolve or disintegrate until the dosage form enters the small intestine.

19. The oral dosage form of claim 18, wherein the enteric coating dissolves at a pH of about 5.5 or above and below a pH of about 6.5.

\* \* \* \* \*